(12) United States Patent
Carney et al.

(10) Patent No.: US 8,952,129 B2
(45) Date of Patent: Feb. 10, 2015

(54) METHOD OF TREATING DEGENERATIVE DISEASES

(75) Inventors: Darrell H. Carney, Dickinson, TX (US); Randolph C. Steer, Rancho Mirage, CA (US)

(73) Assignee: The Board of Regents of the University of Texas System, Austin, TX (US)

( * ) Notice: Subject to any disclaimer, the term of this patent is extended or adjusted under 35 U.S.C. 154(b) by 1095 days.

(21) Appl. No.: 12/934,251

(22) PCT Filed: Mar. 24, 2009

(86) PCT No.: PCT/US2009/001813
§ 371 (c)(1),
(2), (4) Date: Mar. 7, 2011

(87) PCT Pub. No.: WO2009/120300
PCT Pub. Date: Oct. 1, 2009

(65) Prior Publication Data
US 2011/0165142 A1  Jul. 7, 2011

Related U.S. Application Data

(60) Provisional application No. 61/070,852, filed on Mar. 26, 2008.

(51) Int. Cl.
*C07K 4/00* (2006.01)

(52) U.S. Cl.
USPC .......................... 530/326; 530/327; 514/21.4

(58) Field of Classification Search
USPC .......................... 530/326, 327, 324; 514/21.4
IPC ............. C07K 7/08,14/001; A61K 38/03, 38/17
See application file for complete search history.

(56) References Cited

U.S. PATENT DOCUMENTS

| | | | |
|---|---|---|---|
| 5,352,664 A | 10/1994 | Carney et al. | |
| 6,815,416 B2 | 11/2004 | Carney et al. | |
| 6,855,687 B2 | 2/2005 | Carney et al. | |
| 6,861,407 B2 | 3/2005 | Carney | |
| 6,867,190 B2 | 3/2005 | Carney | |
| 6,894,027 B2 | 5/2005 | Carney et al. | |
| 6,914,050 B2 | 7/2005 | Carney et al. | |
| 7,034,001 B2 | 4/2006 | Carney | |
| 7,049,294 B2 | 5/2006 | Carney | |
| 7,214,661 B2 | 5/2007 | Carney | |
| 7,291,596 B2 | 11/2007 | Hobson et al. | |
| 7,378,500 B2 | 5/2008 | Carney | |
| 7,456,250 B2 | 11/2008 | Carney | |
| 7,713,934 B2 | 5/2010 | Carney | |
| 2004/0209819 A1 | 10/2004 | Carney | |
| 2005/0153893 A1 | 7/2005 | Carney | |
| 2008/0241149 A1 | 10/2008 | Carney et al. | |
| 2009/0029923 A1 | 1/2009 | Carney | |
| 2009/0054343 A1 | 2/2009 | Hobson et al. | |
| 2009/0124550 A1 | 5/2009 | Carney | |
| 2009/0304671 A1 | 12/2009 | Carney et al. | |
| 2010/0297100 A1* | 11/2010 | Jang et al. | 424/94.64 |

FOREIGN PATENT DOCUMENTS

| | | |
|---|---|---|
| WO | WO-2004/014937 | 2/2004 |
| WO | WO-2007/035406 | 3/2007 |
| WO | WO-2008/036387 A | 3/2008 |
| WO | WO-2008/100567 | 8/2008 |
| WO | WO-2008/124172 | 10/2008 |
| WO | WO-2008/124173 | 10/2008 |
| WO | WO-2009/038243 | 3/2009 |
| WO | WO-2009/142679 | 11/2009 |

OTHER PUBLICATIONS

Smirnova I. V. (Journal of Neurobiology 48(2), 87-100, 2001).*
Suo Z (Current Drug Targets. Inflammation and Allergy 3(1), 105-114, 2004).*
Sokolova (Thrombosis and Haemostasis 100(4), 576-581, 2008).*
Naldini (Peptides 25(11), 1917-1926, 2004).*
Sower (Experimental Cell Research 247, 422-431, 1999).*
U.S. Appl. No. 12/595,051, filed Apr. 10, 2008, Olszewska-Pazdrak et al.
U.S. Appl. No. 12/595,343, filed Apr. 10, 2008, Olszewska-Pazdrak et al.
U.S. Appl. No. 12/934,366, filed Mar. 24, 2009, Carney et al.
U.S. Appl. No. 12/934,424, filed Mar. 24, 2009, Carney et al.
U.S. Appl. No. 12/934,585, filed Mar. 26, 2009, Steer et al.
Carney, D.H., et al., "Enhancement of Incisional Wound Healing and Neovascularization in Normal Rats by Thrombin and Synthetic Thrombin Receptor-activating Peptides," J. Clin. Invest., 1992, vol. 89, pp. 1469-1477.
Carney, D.H., et al., "Postclotting Cellular Effects of Thrombin Mediated by Interaction with High-Affinity Thrombin Receptors," Thrombin : Structure and Function, 1992, Chapter 10, pp. 351-396.
Carney, D.H., et al., "Role of High-Affinity Thrombin Receptors in Postclotting Cellular Effects of Thrombin," Seminars in Thrombosis and Hemostasis, 1992, vol. 18, pp. 91-102.
Coleman, C.L., et al., "Systemic Injection of Thrombin Peptide TP508 Mitigates Angioplasty-related Restenosis in Hypercholesterolemic Rabbit Iliac Arteries," Abstract LB14, Presented at the Experimental Biology 2001 Meeting (Orlando, Florida).
International Search Report in PCT/US2009/001813, dated Oct. 14, 2009.
Norfleet, et al., "Thrombin Peptide, TP508, Stimulates Angiogenic Responses in Animal Models of Dermal Wound Healing, in Chick Chorioallantoic Membranes, and in Cultured Human Aortic and Microvascular Endothelial Cells," General Pharmacology, Pergamon Press, 2002, vol. 35, pp. 249-254.

*Primary Examiner* — David Lukton
(74) *Attorney, Agent, or Firm* — Mueting, Raasch & Gebhardt, P.A.

(57) ABSTRACT

Agonists of a non-proteolytically activated receptor can be used in methods for treating a disease or disorder in a subject. The methods comprise administering to the subject a therapeutically effective amount of an agonist, wherein the disease or disorder is scleroderma, macular degeneration, diabetic retinopathy, Huntington's disease, Parkinson's disease, closed head trauma, glaucoma, optic neuritis or allograft vasculopathy.

16 Claims, 5 Drawing Sheets

(56) References Cited

OTHER PUBLICATIONS

Olszewska-Pazdrak et al: "Effect of Thrombin Peptide TP508 on Cultured Endothelial Cells Suggest a Wound Healing Mode of Action that Involves Reversal of Endothelial Dysfunction", Wound Repair and Regeneration, vol. 15, Mar. 2007, p. A32.

Olszewska-Pazdrak et al: "TP508 Peptide Restores VEGF-induced Activation of eNOS in Hypoxic Human Endothelial Cells", Arteriosclerosis, Thrombosis, and Vascular Biology, vol. 27, Jun. 2007, p. E-75.

Stiernberg, et al., "Acceleration of Full-Thickness Wound Healing in Normal Rats by the Synthetic Thrombin Peptide, TP508," Wound Repair and Regeneration, Mosby-Year Book, 2000, vol. 8, pp. 204-215.

Stiernberg, J., et al., "The Role of Thrombin and Thrombin Receptor Activating Peptide (TRAP-508) in Initiation of Tissue Repair," Thrombosis and Haemostasis, 1993, vol. 70, pp. 158-162.

\* cited by examiner

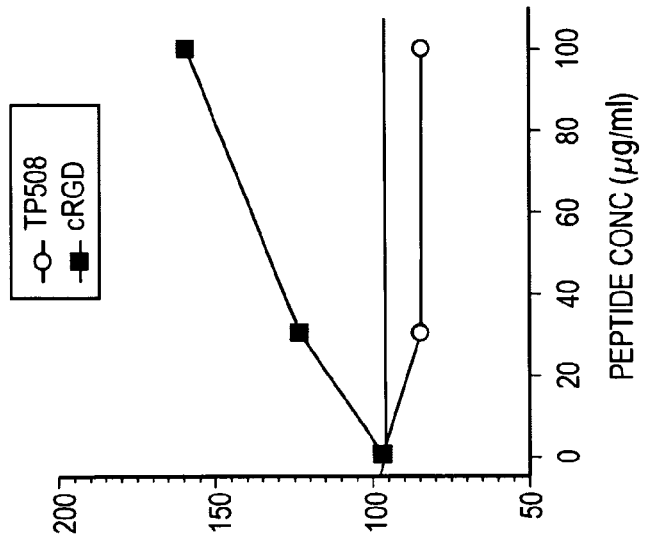
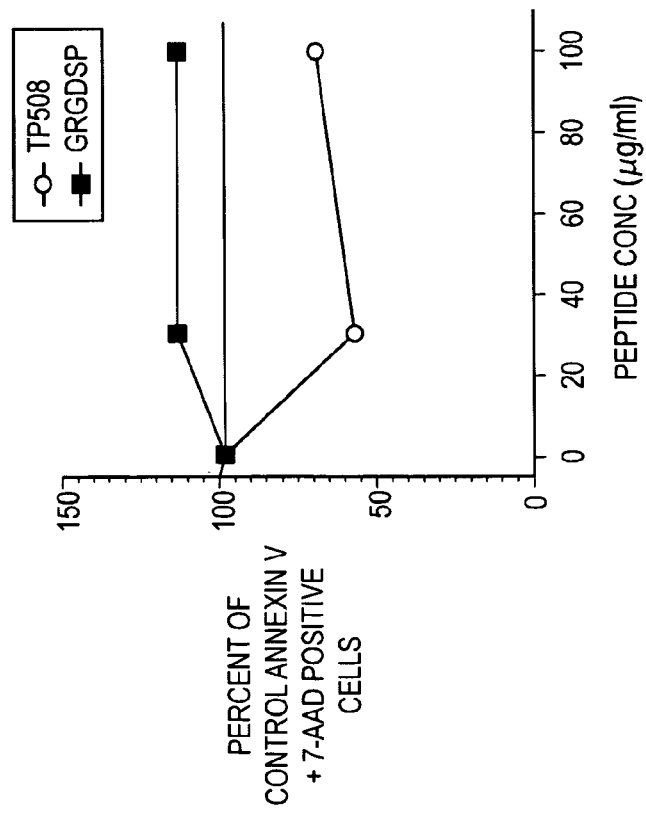
Effect of Peptide Pretreatment (1 hr) on H2O2 Induced Apoptosis
FIG. 2A
FIG. 2B

SEQUENCE LISTING

```
<160> NUMBER OF SEQ ID NOS: 29

<210> SEQ ID NO 1
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (13)..(13)
<223> OTHER INFORMATION: Phe, Met, Leu, His or Val

<400> SEQUENCE: 1

Arg Gly Asp Ala Cys Xaa Gly Asp Ser Gly Gly Pro Xaa Val
1               5                   10

<210> SEQ ID NO 2
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (15)..(15)
<223> OTHER INFORMATION: Glu or Gln
<220> FEATURE:
<221> NAME/KEY: MOD_RES
<222> LOCATION: (22)..(22)
<223> OTHER INFORMATION: Phe, Met, Leu, His or Val
<220> FEATURE:
<223> OTHER INFORMATION: see specification as filed for detailed
      description of substitutions and preferred embodiments

<400> SEQUENCE: 2

Ala Gly Tyr Lys Pro Asp Glu Gly Lys Arg Gly Asp Ala Cys Xaa Gly
1               5                   10                  15

Asp Ser Gly Gly Pro Xaa Val
            20

<210> SEQ ID NO 3
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 3
```

```
Ala Gly Tyr Lys Pro Asp Glu Gly Lys Arg Gly Asp Ala Cys Glu Gly
1               5                   10                  15

Asp Ser Gly Gly Pro Phe Val
            20

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Gly, Ser or S-protected Cys
<220> FEATURE:
<221> NAME/KEY: MOD_RES
<222> LOCATION: (6)..(6)
<223> OTHER INFORMATION: Glu or Gln
<220> FEATURE:
<221> NAME/KEY: MOD_RES
<222> LOCATION: (13)..(13)
<223> OTHER INFORMATION: Phe, Met, Leu, His or Val

<400> SEQUENCE: 4

Arg Gly Asp Ala Xaa Xaa Gly Asp Ser Gly Gly Pro Xaa Val
1               5                   10

<210> SEQ ID NO 5
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Ala, Gly, Ser or S-protected Cys
<220> FEATURE:
<221> NAME/KEY: MOD_RES
<222> LOCATION: (15)..(15)
<223> OTHER INFORMATION: Glu or Gln
<220> FEATURE:
<221> NAME/KEY: MOD_RES
<222> LOCATION: (22)..(22)
<223> OTHER INFORMATION: Phe, Met, Leu, His or Val

<400> SEQUENCE: 5

Ala Gly Tyr Lys Pro Asp Glu Gly Lys Arg Gly Asp Ala Xaa Xaa Gly
1               5                   10                  15

Asp Ser Gly Gly Pro Xaa Val
            20

<210> SEQ ID NO 6
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Gly Tyr Lys Pro Asp Glu Gly Lys Arg Gly Asp Ala Cys Glu Gly
1               5                   10                  15

Asp Ser Gly Gly Pro Phe Val
            20
```

```
<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Glu Gly Lys Arg Gly Asp Ala Cys Glu Gly
1               5                   10

<210> SEQ ID NO 8
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (15)..(15)
<223> OTHER INFORMATION: Glu or Gln
<220> FEATURE:
<221> NAME/KEY: MOD_RES
<222> LOCATION: (22)..(22)
<223> OTHER INFORMATION: Phe, Met, Leu, His or Val
<220> FEATURE:
<223> OTHER INFORMATION: see specification as filed for detailed
      description of substitutions and preferred embodiments

<400> SEQUENCE: 8

Ala Gly Tyr Lys Pro Asp Glu Gly Lys Arg Gly Asp Ala Cys Xaa Gly
1               5                   10                  15

Asp Ser Gly Gly Pro Xaa Val Met Lys Ser Pro Phe Asn Asn Arg Trp
            20                  25                  30

Tyr

<210> SEQ ID NO 9
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<223> OTHER INFORMATION: C-term NH2

<400> SEQUENCE: 9

Ala Gly Tyr Lys Pro Asp Glu Gly Lys Arg Gly Asp Ala Cys Glu Gly
1               5                   10                  15

Asp Ser Gly Gly Pro Phe Val Met Lys Ser Pro Phe Asn Asn Arg Trp
            20                  25                  30

Tyr

<210> SEQ ID NO 10
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Glu or Gln
```

```
<220> FEATURE:
<221> NAME/KEY: MOD_RES
<222> LOCATION: (11)..(11)
<223> OTHER INFORMATION: Phe, Met, Leu, His or Val

<400> SEQUENCE: 10

Asp Ala Cys Xaa Gly Asp Ser Gly Gly Pro Xaa Val
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Ala, Gly, Ser or S-protected Cys

<400> SEQUENCE: 11

Arg Gly Asp Ala Xaa Glu Gly Asp Ser Gly Gly Pro Phe Val
1               5                   10

<210> SEQ ID NO 12
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<221> NAME/KEY: MOD_RES
<222> LOCATION: (15)..(15)
<223> OTHER INFORMATION: Glu or Gln
<220> FEATURE:
<221> NAME/KEY: MOD_RES
<222> LOCATION: (22)..(22)
<223> OTHER INFORMATION: Phe, Met, Leu, His or Val
<220> FEATURE:
<223> OTHER INFORMATION: C-term NH2

<400> SEQUENCE: 12

Ala Gly Tyr Lys Pro Asp Glu Gly Lys Arg Gly Asp Ala Cys Xaa Gly
1               5                   10                  15

Asp Ser Gly Gly Pro Xaa Val
            20

<210> SEQ ID NO 13
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Ala or Ser
<220> FEATURE:
<221> NAME/KEY: MOD_RES
<222> LOCATION: (4)..(4)
<223> OTHER INFORMATION: Glu or Gln
<220> FEATURE:
<221> NAME/KEY: MOD_RES
<222> LOCATION: (11)..(11)
<223> OTHER INFORMATION: Phe, Met, Leu, His or Val

<400> SEQUENCE: 13
```

```
Asp Xaa Cys Xaa Gly Asp Ser Gly Gly Pro Xaa Val
1               5                   10
```

<210> SEQ ID NO 14
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 14

```
Cys Glu Gly Asp Ser Gly Gly Pro Phe Val
1               5                   10
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Glu or Gln
<220> FEATURE:
<221> NAME/KEY: MOD_RES
<222> LOCATION: (9)..(9)
<223> OTHER INFORMATION: Phe, Met, Leu, His or Val

<400> SEQUENCE: 15

```
Cys Xaa Gly Asp Ser Gly Gly Pro Xaa Val
1               5                   10
```

<210> SEQ ID NO 16
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

```
Arg Gly Asp Ala
1
```

<210> SEQ ID NO 17
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

```
Arg Gly Asp Ala Cys Glu Gly Asp Ser Gly Gly Pro Phe Val
1               5                   10
```

<210> SEQ ID NO 18
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

```
Asp Asn Met Phe Cys Ala Gly Tyr Lys Pro Asp Glu Gly Lys Arg Gly
1               5                   10                  15

Asp Ala Cys Glu Gly Asp Ser Gly Gly Pro Phe Val Met Lys Ser Pro
            20                  25                  30

Phe

<210> SEQ ID NO 19
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (20)..(20)
<223> OTHER INFORMATION: Glu or Gln
<220> FEATURE:
<221> NAME/KEY: MOD_RES
<222> LOCATION: (27)..(27)
<223> OTHER INFORMATION: Phe, Met, Leu, His or Val

<400> SEQUENCE: 19

Asp Asn Met Phe Cys Ala Gly Tyr Lys Pro Asp Glu Gly Lys Arg Gly
1               5                   10                  15

Asp Ala Cys Xaa Gly Asp Ser Gly Gly Pro Xaa Val Met Lys Ser Pro
            20                  25                  30

Phe

<210> SEQ ID NO 20
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (14)..(14)
<223> OTHER INFORMATION: Ala, Gly, Ser or S-protected Cys

<400> SEQUENCE: 20

Ala Gly Tyr Lys Pro Asp Glu Gly Lys Arg Gly Asp Ala Xaa Glu Gly
1               5                   10                  15

Asp Ser Gly Gly Pro Phe Val
            20

<210> SEQ ID NO 21
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Ala Gly Tyr Lys Pro Asp Glu Gly Lys Arg Gly Asp Ala Ala Glu Gly
1               5                   10                  15

Asp Ser Gly Gly Pro Phe Val
            20

<210> SEQ ID NO 22
<211> LENGTH: 23
<212> TYPE: PRT
<213> ORGANISM: Artificial Sequence
<220> FEATURE:
```

```
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

<400> SEQUENCE: 22

Ala Gly Tyr Lys Pro Asp Glu Gly Lys Arg Gly Asp Ala Ala Glu Gly
1               5                   10                  15

Asp Ser Gly Gly Pro Phe Val
            20

<210> SEQ ID NO 23
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Ala, Gly, Ser or S-protected Cys
<220> FEATURE:
<221> NAME/KEY: MOD_RES
<222> LOCATION: (19)..(19)
<223> OTHER INFORMATION: Ala, Gly, Ser or S-protected Cys
<220> FEATURE:
<223> OTHER INFORMATION: see specification as filed for detailed
      description of substitutions and preferred embodiments

<400> SEQUENCE: 23

Asp Asn Met Phe Xaa Ala Gly Tyr Lys Pro Asp Glu Gly Lys Arg Gly
1               5                   10                  15

Asp Ala Xaa Glu Gly Asp Ser Gly Gly Pro Phe Val Met Lys Ser Pro
            20                  25                  30

Phe

<210> SEQ ID NO 24
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (5)..(5)
<223> OTHER INFORMATION: Ala, Gly, Ser or S-protected Cys
<220> FEATURE:
<221> NAME/KEY: MOD_RES
<222> LOCATION: (19)..(19)
<223> OTHER INFORMATION: Ala, Gly, Ser or S-protected Cys
<220> FEATURE:
<221> NAME/KEY: MOD_RES
<222> LOCATION: (20)..(20)
<223> OTHER INFORMATION: Glu or Gln
<220> FEATURE:
<221> NAME/KEY: MOD_RES
<222> LOCATION: (27)..(27)
<223> OTHER INFORMATION: Phe, Met, Leu, His or Val
<220> FEATURE:
<223> OTHER INFORMATION: see specification as filed for detailed
      description of substitutions and preferred embodiments

<400> SEQUENCE: 24

Asp Asn Met Phe Xaa Ala Gly Tyr Lys Pro Asp Glu Gly Lys Arg Gly
1               5                   10                  15
```

Asp Ala Xaa Xaa Gly Asp Ser Gly Gly Pro Xaa Val Met Lys Ser Pro
            20                  25                  30

Phe

<210> SEQ ID NO 25
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

Asp Asn Met Phe Ala Ala Gly Tyr Lys Pro Asp Glu Gly Lys Arg Gly
1               5                   10                  15

Asp Ala Ala Glu Gly Asp Ser Gly Gly Pro Phe Val Met Lys Ser Pro
            20                  25                  30

Phe

<210> SEQ ID NO 26
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: N-term H
<220> FEATURE:
<223> OTHER INFORMATION: C-term NH2

<400> SEQUENCE: 26

Asp Asn Met Phe Ala Ala Gly Tyr Lys Pro Asp Glu Gly Lys Arg Gly
1               5                   10                  15

Asp Ala Ala Glu Gly Asp Ser Gly Gly Pro Phe Val Met Lys Ser Pro
            20                  25                  30

Phe

<210> SEQ ID NO 27
<211> LENGTH: 33
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ala Gly Tyr Lys Pro Asp Glu Gly Lys Arg Gly Asp Ala Cys Glu Gly
1               5                   10                  15

Asp Ser Gly Gly Pro Phe Val Met Lys Ser Pro Phe Asn Asn Arg Trp
            20                  25                  30

Tyr

<210> SEQ ID NO 28
<211> LENGTH: 23
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: N-term H
<220> FEATURE:
<223> OTHER INFORMATION: C-term NH2

-continued

```
<400> SEQUENCE: 28

Ala Gly Tyr Lys Pro Asp Glu Gly Lys Arg Gly Asp Ala Ser Glu Gly
1               5                   10                  15

Asp Ser Gly Gly Pro Phe Val
            20

<210> SEQ ID NO 29
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Arg Gly Asp Ser Pro
1               5
```

METHOD OF TREATING DEGENERATIVE DISEASES

RELATED APPLICATION

This application is the U.S. National Stage of PCT International Application Number PCT/US2009/001813, filed Mar. 24, 2009, which claims the benefit of U.S. Provisional Application No. 61/070,852, filed on Mar. 26, 2008. The entire teachings of the above applications are incorporated herein by reference.

SEQUENCE LISTING

The instant application contains a Sequence Listing which has been submitted in ASCII format via EFS-Web and is hereby incorporated by reference in its entirety. Said ASCII copy, created on Nov. 9, 2010, is named 09661201.txt and is 13,079 bytes in size.

BACKGROUND OF THE INVENTION

Many diseases or disorders have chronic and/or progressive effects that can occur over a period of years. Degeneration of function occurs with deterioration of the involved tissues.

Huntington's disease is a genetic degenerative brain disorder characterized by chorea and behavioral disturbance.

Parkinson's disease is a chronic, progressive disorder in which patients may display rigidity, tremor and bradykinesia. Patients are frequently disabled by the symptoms.

Macular degeneration is the leading cause of blindness in people over 65 years old.

Diabetic retinopathy is a common consequence in diabetics and is a leading cause of blindness in the growing population of diabetics.

Scleroderma is a chronic multisystem disorder characterized by accumulation of connective tissue in the skin and in visceral organs.

Optic neuritis results from inflammation of the optic nerve that can cause loss of vision.

Glaucoma is a progressive optic neuropathy usually associated with elevated intraocular pressure.

The incidence of allograft vasculopathy (transplant vasculopathy or transplant coronary artery disease) increases in the years following heart transplant. Allograft vasculopathy kills about 40% of heart transplant patients.

Closed head trauma includes concussion and contusion, for example, and can be severe enough to result in prolonged or irreversible brain damage.

Treatments to reverse, slow or arrest progression of degenerative conditions would add to quality and extent of life in patients afflicted with a degenerative disease or disorder.

SUMMARY OF THE INVENTION

Agonists of a non-proteolytically activated receptor (NPAR) can be used in methods for treating a disease or disorder in a subject. The methods comprise administering to the subject a therapeutically effective amount of one or more such agonists, wherein the disease or disorder is scleroderma, macular degeneration, diabetic retinopathy, Huntington's disease, Parkinson's disease, closed head trauma, glaucoma, optic neuritis or allograft vasculopathy. NPAR agonists may exert their effect by inhibiting apoptosis. NPAR agonists can be thrombin peptide derivatives.

The thrombin peptide derivatives to be used in the methods comprise amino acid sequences identical to, or similar to, a region of thrombin. Usually the thrombin peptide derivatives are 12-23 amino acid residues in length. In some cases, the thrombin peptide derivatives are dimers, and in particular, dimers that result from formation of a disulfide bond between two cysteine residues of peptide monomers.

BRIEF DESCRIPTION OF THE DRAWINGS

FIG. 2A and FIG. 2B are graphs of Annexin V and 7-AAD (7-amino-actinomycin D) positive cells (indicating apoptosis), in mouse fibroblasts grown in serum-free medium and treated with either TP508 or peptide GRGDSP (SEQ ID NO:29) (FIG. 2A) or peptide cRGD (FIG. 2B), followed by $H_2O_2$ treatment.

DETAILED DESCRIPTION OF THE INVENTION

Figure 1:
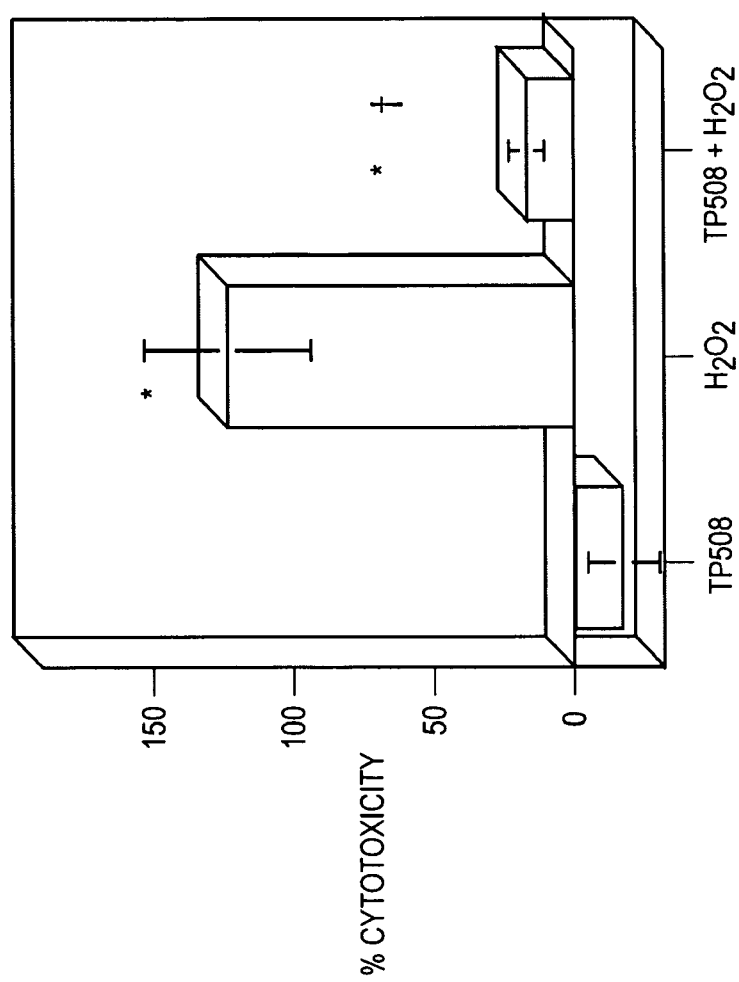
FIG. 1 is a bar graph showing the extent of the cytotoxic effect of 100 mM $H_2O_2$ on human umbilical vein endothelial cells treated or not treated with TP508.

Compounds which stimulate a non-proteolytically activated thrombin receptor (NPAR) are said to be NPAR agonists. One such NPAR is a high-affinity thrombin receptor present on the surface of most cells. This NPAR component is largely responsible for high-affinity binding of thrombin, proteolytically inactivated thrombin, and thrombin derived peptides to cells. This NPAR appears to mediate a number of cellular signals that are initiated by thrombin independent of its proteolytic activity (see Sower, et. al., *Experimental Cell Research* 247:422 (1999)). This NPAR is therefore characterized by its high affinity interaction with thrombin at cell surfaces and its activation by proteolytically inactive derivatives of thrombin and thrombin derived peptide agonists as described below. NPAR activation can be assayed based on the ability of molecules to stimulate cell proliferation when added to fibroblasts in the presence of submitogenic concentrations of thrombin or molecules that activate protein kinase C, as disclosed in U.S. Pat. Nos. 5,352,664 and 5,500,412. The entire teachings of these patents are incorporated herein by reference. NPAR agonists can be identified by this activation or by their ability to compete with $^{125}$I-thrombin binding to cells.

One or more NPAR agonists, and in particular, one or more thrombin peptide derivatives, can be used in methods to treat any of the following: scleroderma, macular degeneration, diabetic retinopathy, Huntington's disease, Parkinson's disease, closed head trauma, glaucoma, optic neuritis, and allograft vasculopathy. Compositions comprising NPAR agonists can be administered to a subject in need of treatment of the diseases and disorders described herein. Treatment can ameliorate the disease or disorder, or alleviate the symptoms thereof. NPAR agonists can be administered to subjects who can benefit from therapeutic intervention causing complete or partial alleviation of symptoms. NPAR agonists can be administered to subjects, (e.g., human patients) at risk for developing a disorder described herein, to reduce the probability of developing the disorder. For example, treatment can cause a reduction in the probability of developing the disorder by up to 20, 30, 40, 50, 60, 70, 80, or 90 percent. Treatment can in some cases, delay the development of a disorder, reduce symptoms, or delay severity of symptoms.

Additional embodiments of the invention relate to the administration of a thrombin peptide derivative, for example, as part of a pharmaceutical composition, comprising a pharmaceutically acceptable carrier, to achieve any of the physiological effects discussed herein.

A thrombin receptor binding domain is defined as a polypeptide or portion of a polypeptide which directly binds to the thrombin receptor and/or competitively inhibits binding between high-affinity thrombin receptors and alpha-thrombin. In one embodiment, the thrombin receptor binding domain or portion thereof comprises the amino acid sequence Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). Another portion of a thrombin receptor binding domain comprises the amino acid sequence Glu-Gly-Lys-Arg-Gly-Asp-Ala-Cys-Glu-Gly (SEQ ID NO:7).

NPAR agonists of the present invention include thrombin peptide derivatives, modified thrombin peptide derivatives and thrombin peptide derivative dimers as disclosed herein.

Thrombin Peptide Derivatives

Among NPAR agonists are thrombin peptide derivatives, which are analogs of thrombin that have an amino acid sequence derived at least in part from that of thrombin and are active at a non-proteolytically activated thrombin receptor. Thrombin peptide derivatives include, for example, peptides that are produced by recombinant DNA methods, peptides produced by enzymatic digestion of thrombin, and peptides produced synthetically, which can comprise amino acid substitutions compared to thrombin, and/or modified amino acid residues, especially at the termini.

NPAR agonists of the present invention include thrombin derivative peptides described in U.S. Pat. Nos. 5,352,664 and 5,500,412. In one embodiment, the NPAR agonist of the present invention is a thrombin peptide derivative or a physiologically functional equivalent, i.e., a polypeptide with no more than about fifty amino acid residues, preferably no more than about thirty amino acid residues and having sufficient homology to the fragment of human thrombin corresponding to thrombin amino acid residues 508-530 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val; SEQ ID NO:6) that the polypeptide activates NPAR. The thrombin peptide derivatives or modified thrombin peptide derivatives described herein preferably have from about 12 to about 23 amino acid residues, more preferably from about 19 to about 23 amino acid residues.

In another embodiment, the NPAR agonist of the present invention is a thrombin peptide derivative comprising a moiety represented by Structural Formula (I):

Asp-Ala-R (I).

R is a serine esterase conserved domain. Serine esterases (e.g., trypsin, thrombin, chymotrypsin and the like) have a region that is highly conserved. "Serine esterase conserved domain" refers to a polypeptide having the amino acid sequence of one of these conserved regions or is sufficiently homologous to one of these conserved regions such that the thrombin peptide derivative retains NPAR activating ability.

A physiologically functional equivalent of a thrombin derivative encompasses molecules which differ from thrombin derivatives in particulars which do not affect the function of the thrombin receptor binding domain or the serine esterase conserved amino acid sequence. Such particulars may include, but are not limited to, conservative amino acid substitutions and modifications, for example, amidation of the carboxyl terminus, acetylation of the amino terminus, conjugation of the polypeptide to a physiologically inert carrier molecule, or sequence alterations in accordance with the serine esterase conserved sequences.

A domain having a serine esterase conserved sequence can comprise a polypeptide sequence containing 4-12 of the N-terminal amino acid residues of the dodecapeptide previously shown to be highly conserved among serine proteases (Asp-$X_1$-Cys-$X_2$-Gly-Asp-Ser-Gly-Gly-Pro-$X_3$-Val; SEQ ID NO:13); wherein $X_1$ is either Ala or Ser; $X_2$ is either Glu or Gln; and $X_3$ is Phe, Met, Leu, His, or Val.

In one embodiment, the serine esterase conserved sequence comprises the amino acid sequence Cys-Glu-Gly-Asp-Ser-Gly-Gly-Pro-Phe-Val (SEQ ID NO:14) or a C-terminal truncated fragment of a polypeptide having the amino acid sequence of SEQ ID NO:14. It is understood, however, that zero, one, two or three amino acid residues in the serine esterase conserved sequence can differ from the corresponding amino acid in SEQ ID NO:14. Preferably, the amino acid residues in the serine esterase conserved sequence which differ from the corresponding amino acid in SEQ ID NO:14 are conservative substitutions, and are more preferably highly conservative substitutions. A "C-terminal truncated fragment" refers to a fragment remaining after removing an amino acid residue or block of amino acid residues from the C-terminus, said fragment having at least six and more preferably at least nine amino acid residues.

In another embodiment, the serine esterase conserved sequence comprises the amino acid sequence of SEQ ID NO:15 (Cys-$X_1$-Gly-Asp-Ser-Gly-Gly-Pro-$X_2$-Val; $X_1$ is Glu or Gln and $X_2$ is Phe, Met, Leu, His or Val) or a C-terminal truncated fragment thereof having at least six amino acid residues, preferably at least nine amino acid residues.

In a preferred embodiment, the thrombin peptide derivative comprises a serine esterase conserved sequence and a polypeptide having a more specific thrombin amino acid sequence Arg-Gly-Asp-Ala (SEQ ID NO:16). One example of a thrombin peptide derivative of this type comprises Arg-Gly-Asp-Ala-Cys-$X_1$-Gly-Asp-Ser-Gly-Gly-Pro-$X_2$-Val (SEQ ID NO:1). $X_1$ and $X_2$ are as defined above. The thrombin peptide derivative can comprise the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6), or an N-terminal truncated fragment thereof, provided that zero, one, two or three amino acid residues at positions 1-9 in the thrombin peptide derivative differ from the amino acid residue at the corresponding position of SEQ ID NO:6. Preferably, the amino acid residues in the thrombin peptide derivative which differ from the corresponding amino acid residues in SEQ ID NO:6 are conservative substitutions, and are more preferably highly conservative substitutions. An "N-terminal truncated fragment" refers to a fragment remaining after removing an amino acid residue or block of amino acid residues from the N-terminus, preferably a block of no more than six amino acid residues, more preferably a block of no more than three amino acid residues.

Optionally, the thrombin peptide derivatives described herein can be amidated at the C-terminus and/or acylated at the N-terminus. In a specific embodiment, the thrombin peptide derivatives comprise a C-terminal amide and optionally comprise an acylated N-terminus, wherein said C-terminal amide is represented by —C(O)NR$_a$R$_b$, wherein R$_a$ and R$_b$ are independently hydrogen, a substituted or unsubstituted aliphatic group comprising up to 10 carbon atoms, or R$_a$ and R$_b$, taken together with the nitrogen to which they are bonded, form a C$_3$-C$_{10}$ non-aromatic heterocyclic group, and said N-terminal acyl group is represented by R$_c$C(O)—, wherein R$_c$ is hydrogen, a substituted or unsubstituted aliphatic group comprising up to 10 carbon atoms, or a C$_3$-C$_{10}$ substituted or unsubstituted aromatic group. In another specific embodiment, the N-terminus of the thrombin peptide derivative is free (i.e., unsubstituted) and the C-terminus is free (i.e., unsubstituted) or amidated, preferably as a carboxamide (i.e., —C(O)NH$_2$). In a specific embodiment, the thrombin peptide derivative comprises the following amino acid sequence: Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6). In another specific embodiment, the thrombin peptide derivative comprises the amino sequence of Arg-Gly-Asp-Ala-Cys-Glu-Gly-Asp-Ser-Gly-Gly-Pro-Phe-Val (SEQ ID NO:17). Alternatively, the thrombin peptide derivative comprises the amino acid sequence of SEQ ID NO:18: Asp-Asn-Met-Phe-Cys-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe. The thrombin peptide derivatives comprising the amino acid sequences SEQ ID NO: 6, 17, or 18 can optionally be amidated at the C-terminus and/or acylated at the N-terminus. Preferably, the N-terminus is free (i.e., unsubstituted) and the C-terminus is free (i.e., unsubstituted) or amidated, preferably a carboxamide (i.e., —C(O)NH$_2$). It is understood, however, that zero, one, two or three amino acid residues at positions 1-9 and 14-23 in the thrombin peptide derivative can differ from the corresponding amino acid in SEQ ID NO:6. It is also understood that zero, one, two or three amino acid residues at positions 1-14 and 19-33 in the thrombin peptide derivative can differ from the corresponding amino acid in SEQ ID NO:18. Preferably, the amino acid residues in the thrombin peptide derivative which differ from the corresponding amino acid in SEQ ID NO:6 or SEQ ID NO:18 are conservative substitutions, and are more preferably highly conservative substitutions. Alternatively, an N-terminal truncated fragment of the thrombin peptide derivative having at least fourteen amino acid residues or a C-terminal truncated fragment of the thrombin peptide derivative having at least eighteen amino acid residues is a thrombin peptide derivative to be used as an NPAR agonist.

A "C-terminal truncated fragment" refers to a fragment remaining after removing an amino acid or block of amino acid residues from the C-terminus. An "N-terminal truncated fragment" refers to a fragment remaining after removing an amino acid residue or block of amino acid residues from the N-terminus. It is to be understood that both C-terminal truncated fragments and N-terminal truncated fragments can optionally be amidated at the C-terminus and/or acylated at the N-terminus.

A preferred thrombin peptide derivative for use in the disclosed methods comprises the polypeptide Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2). Another preferred thrombin peptide derivative for use in the disclosed method comprises the polypeptide Asp-Asn-Met-Phe-Cys-Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val-Met-Lys-Ser-Pro-Phe (SEQ ID NO:19). X$_1$ is Glu or Gln; X$_2$ is Phe, Met, Leu, His or Val. The thrombin peptide derivatives of SEQ ID NO:2 and SEQ ID NO:19 can optionally comprise a C-terminal amide and/or acylated N-terminus, as defined above. Preferably, the N-terminus is free (i.e., unsubstituted) and the C-terminus is free (i.e., unsubstituted) or amidated, preferably as a carboxamide (i.e., —C(O)NH$_2$). Alternatively, N-terminal truncated fragments of these preferred thrombin peptide derivatives, the N-terminal truncated fragments having at least fourteen amino acid residues, or C-terminal truncated fragments of these preferred thrombin peptide derivatives, the C-terminal truncated fragments having at least eighteen amino acid residues, can also be used in the disclosed methods.

TP508 is an example of a thrombin peptide derivative and is 23 amino acid residues long, wherein the N-terminal amino acid residue Ala is unsubstituted and the COOH of the C-terminal amino acid Val is modified to an amide represented by —C(O)NH$_2$ (SEQ ID NO:3). Another example of a thrombin peptide derivative comprises the amino acid sequence of SEQ ID NO:6, wherein both N- and C-termini are unsubstituted ("deamide TP508"). Other examples of thrombin peptide derivatives which can be used in the disclosed method include N-terminal truncated fragments of TP508 (or deamide TP508), the N-terminal truncated fragments having at least fourteen amino acid residues, or C-terminal truncated fragments of TP508 (or deamide TP508), the C-terminal truncated fragments having at least eighteen amino acid residues.

As used herein, a "conservative substitution" in a polypeptide is the replacement of an amino acid with another amino acid that has the same net electronic charge and approximately the same size and shape. Amino acid residues with aliphatic or substituted aliphatic amino acid side chains have approximately the same size when the total number of carbon and heteroatoms in their side chains differs by no more than about four. They have approximately the same shape when the number of branches in their side chains differs by no more than one. Amino acid residues with phenyl or substituted phenyl groups in their side chains are considered to have about the same size and shape. Listed below are five groups of amino acids. Replacing an amino acid residue in a polypeptide with another amino acid residue from the same group results in a conservative substitution:

Group I: glycine, alanine, valine, leucine, isoleucine, serine, threonine, cysteine, and non-naturally occurring amino acids with C1-C4 aliphatic or C1-C4 hydroxyl substituted aliphatic side chains (straight chained or monobranched).

Group II: glutamic acid, aspartic acid and non-naturally occurring amino acids with carboxylic acid substituted C1-C4 aliphatic side chains (unbranched or one branch point).

Group III: lysine, ornithine, arginine and non-naturally occurring amino acids with amine or guanidino substituted C1-C4 aliphatic side chains (unbranched or one branch point).

Group IV: glutamine, asparagine and non-naturally occurring amino acids with amide substituted C1-C4 aliphatic side chains (unbranched or one branch point).

Group V: phenylalanine, phenylglycine, tyrosine and tryptophan.

As used herein, a "highly conservative substitution" in a polypeptide is the replacement of an amino acid with another amino acid that has the same functional group in the side chain and nearly the same size and shape. Amino acids with aliphatic or substituted aliphatic amino acid side chains have nearly the same size when the total number of carbon and heteroatoms in their side chains differs by no more than two. They have nearly the same shape when they have the same number of branches in their side chains. Examples of highly conservative substitutions include valine for leucine, threonine for serine, aspartic acid for glutamic acid and phenylglycine for phenylalanine. Examples of substitutions which are not highly conservative include alanine for valine, alanine for serine and aspartic acid for serine.

Modified Thrombin Peptide Derivatives

In one embodiment of the invention, the NPAR agonists are modified relative to the thrombin peptide derivatives described above, wherein cysteine residues of aforementioned thrombin peptide derivatives are replaced with amino acids having similar size and charge properties to minimize dimerization of the peptides. Examples of suitable amino acids include alanine, glycine, serine, and an S-protected cysteine. Preferably, cysteine is replaced with alanine or serine. The modified thrombin peptide derivatives have about the same biological activity as the unmodified thrombin peptide derivatives.

It will be understood that the modified thrombin peptide derivatives disclosed herein can optionally comprise C-terminal amides and/or N-terminal acyl groups, as described above. Preferably, the N-terminus of a thrombin peptide derivative is free (i.e., unsubstituted) and the C-terminus is free (i.e., unsubstituted) or amidated, preferably as a carboxamide (i.e., —C(O)NH$_2$).

In a specific embodiment, the modified thrombin peptide derivative comprises a polypeptide Arg-Gly-Asp-Ala-Xaa-X$_1$-Gly-Asp-Ser-Gly-Gly-Pro-X$_2$-Val (SEQ ID NO:4), or a C-terminal truncated fragment thereof having at least six amino acids. More specifically, the thrombin peptide derivative comprises the polypeptide Ala-Gly-Tyr-Lys-Pro-Asp-Glu-Gly-Lys-Arg-Gly-Asp-Ala-Xaa-Glu-Gly-Asp-Ser-Gly-Gly-Pro-Phe-Val (SEQ ID NO:20), or a fragment thereof comprising amino acid residues 10-18 of SEQ ID NO:20. Even more specifically, the thrombin peptide derivative comprises the polypeptide Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val (SEQ ID NO:5), or a fragment thereof comprising amino acid residues 10-18 of SEQ ID NO:5. Xaa is alanine, glycine, serine or an S-protected cysteine. X$_1$ is Glu or Gln and X$_2$ is Phe, Met, Leu, His or Val. In one embodiment, X$_1$ is Glu, X$_2$ is Phe, and Xaa is Ala. In another embodiment, X$_1$ is Glu, X$_2$ is Phe, and Xaa is Ser. One example of a thrombin peptide derivative of this type is the polypeptide Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val (SEQ ID NO:21). A further example of a thrombin peptide derivative of this type is the polypeptide H-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-NH$_2$ (SEQ ID NO:22), wherein H is a hydrogen atom of alanine indicating no modification at the N-terminus, and NH$_2$ indicates amidation at the C-terminus as —C(O)NH$_2$. Zero, one, two or three amino acids in the thrombin peptide derivative differ from the amino acid at the corresponding position of SEQ ID NO:4, 20, 5, 21 or 22, provided that Xaa is alanine, glycine, serine and an S-protected cysteine. Preferably, the difference is conservative.

In another specific embodiment, the thrombin peptide derivative comprises the polypeptide Asp-Asn-Met-Phe-Xbb-Ala-Gly-Tyr-Lys-Pro-Asp-Glu-Gly-Lys-Arg-Gly-Asp-Ala-Xaa-Glu-Gly-Asp-Ser-Gly-Gly-Pro-Phe-Val-Met-Lys-Ser-Pro-Phe (SEQ ID NO:23), or a fragment thereof comprising amino acids 6-28. More preferably, the thrombin peptide derivative comprises the polypeptide Asp-Asn-Met-Phe-Xbb-Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val-Met-Lys-Ser-Pro-Phe (SEQ ID NO:24), or a fragment thereof comprising amino acids 6-28. Xaa and Xbb are independently alanine, glycine, serine or an S-protected cysteine. X$_1$ is Glu or Gln and X$_2$ is Phe, Met, Leu, His or Val. Preferably X$_1$ is Glu, X$_2$ is Phe, and Xaa and Xbb are alanine. One example of a thrombin peptide derivative of this type is a polypeptide comprising the amino acid sequence Asp-Asn-Met-Phe-Ala-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-Met-Lys-Ser-Pro-Phe (SEQ ID NO:25). A further example of a thrombin peptide derivative of this type is the polypeptide H-Asp-Asn-Met-Phe-Ala-Ala-Gly-Tyr-Lys-Pro-Asp-Glu-Gly-Lys-Arg-Gly-Asp-Ala-Ala-Glu-Gly-Asp-Ser-Gly-Gly-Pro-Phe-Val-Met-Lys-Ser-Pro-Phe-NH$_2$ (SEQ ID NO:26), wherein H is a hydrogen atom of aspartic acid indicating no modification at the N-terminus, and NH$_2$ indicates amidation at the C-terminus as —C(O)NH$_2$. Zero, one, two or three amino acids in the thrombin peptide derivative can differ from the amino acid at the corresponding position of SEQ ID NO:23, 24, 25 or 26. Xaa and Xbb are independently alanine, glycine, serine or an S-protected cysteine. Preferably, the difference is conservative.

An "S-protected cysteine" is a cysteine residue in which the reactivity of the thiol moiety, —SH, is blocked with a protecting group. Suitable protecting groups are known in the art and are disclosed, for example, in T. W. Greene and P. G. M. Wuts, *Protective Groups in Organic Synthesis*, 3$^{rd}$ Edition, John Wiley & Sons, (1999), pp. 454-493, the teachings of which are incorporated herein by reference in their entirety. Suitable protecting groups should be non-toxic, stable in pharmaceutical formulations and have minimum additional functionality to maintain the activity of the thrombin peptide derivative. A free thiol can be protected as a thioether, a thioester, or can be oxidized to an unsymmetrical disulfide. Preferably the thiol is protected as a thioether. Suitable thioethers include, but are not limited to, S-alkyl thioethers (e.g., C$_1$-C$_5$ alkyl), and S-benzyl thioethers (e.g., cysteine-S—S-t-Bu). Preferably the protective group is an alkyl thioether. More preferably, the S-protected cysteine is an S-methyl cysteine. Alternatively, the protecting group can be: 1) a cysteine or a cysteine-containing peptide (the "protecting peptide") attached to the cysteine thiol group of the thrombin peptide derivative by a disulfide bond; or 2) an amino acid or peptide ("protecting peptide") attached by a thioamide bond between the cysteine thiol group of the thrombin peptide derivative and a carboxylic acid in the protecting peptide (e.g., at the C-terminus or side chain of aspartic acid or glutamic acid). The protecting peptide can be physiologically inert (e.g., a polyglycine or polyalanine of no more than about fifty amino acids optionally interrupted by a cysteine), or can have a desirable biological activity.

The thrombin peptide derivatives or the modified thrombin peptide derivatives of the present invention can be mixed with a dimerization inhibitor for the preparation of a pharmaceutical composition comprising the thrombin peptide derivatives or the modified thrombin peptide derivatives of the present invention. Dimerization inhibitors can include chelating agents and/or thiol-containing compounds. An antioxidant can also be used in combination with the chelating agent and/or the thiol-containing compound.

A "chelating agent," as used herein, is a compound having multiple sites (two, three, four or more) which can simultaneously bind to a metal ion or metal ions such as, for example, lead, cobalt, iron or copper ions. The binding sites typically comprise oxygen, nitrogen, sulfur or phosphorus. For example, salts of EDTA (ethylenediaminetetraacetic acid) can form at least four to six bonds with a metal ion or metal ions via the oxygen atoms of four acetic acid moieties (—$CH_2C(O)O^-$) and the nitrogen atoms of ethylenediamine moieties (>N—$CH_2$—$CH_2$—$N_<$) of EDTA. It is understood that a chelating agent also includes a polymer which has multiple binding sites to a metal or metal ions. Preferably, a chelating agent of the invention is non-toxic and does not cause unacceptable side effects at the dosages of pharmaceutical composition being administered in the methods of the invention. As a chelating agent of the invention, a copper-chelating agent is preferable. A "copper-chelating agent" refers to a chelating agent which can bind to a copper ion or copper ions. Examples of the copper-chelating agent include ethylenediaminetetraacetic acid (EDTA), penicillamine, trientine, N,N'-diethyldithiocarbamate (DDC), 2,3,2'-tetraamine (2,3,2'-tet), neocuproine, N,N,N',N'-tetrakis(2-pyridylmethyl)ethylenediamine (TPEN), 1,10-phenanthroline (PHE), tetraethylenepentamine (TEPA), triethylenetetraamine and tris(2-carboxyethyl) phosphine (TCEP). Additional chelating agents are diethylenetriaminepentacetic acid (DTPA) and bathophenanthroline disulfonic acid (BPADA). EDTA is a preferred chelating agent. Typical amounts of a chelating agent present in the pharmaceutical compositions of the instant invention are in a range of between about 0.00001% and about 0.1% by weight, preferably between about 0.0001% and about 0.05% by weight.

A "pharmaceutically acceptable thiol-containing compound" as used herein is a compound which comprises at least one thiol (—SH) group and which does not cause unacceptable side effects at the dosages which are being administered. Examples of a pharmaceutically acceptable thiol-containing compound include thioglycerol, mercaptoethanol, thioglycol, thiodiglycol, cysteine, thioglucose, dithiothreitol (DTT) and dithio-bis-maleimidoethane (DTME). Typically, between about 0.001% and about 5% by weight, preferably between about 0.0 5% and about 1.0% by weight of a pharmaceutically acceptable thiol-containing compound is present in the pharmaceutical compositions of the invention.

An "antioxidant," as used herein, is a compound which is used to prevent or reduce an oxidation reaction caused by an oxidizing agent such as oxygen. Examples of antioxidants include tocopherol, cystine, methionine, glutathione, tocotrienol, dimethyl glycine, betaine, butylated hydroxyanisole, butylated hydroxytoluene, vitamin E, ascorbic acid, ascorbyl palmitate, thioglycolic acid and antioxidant peptides such as, for example, turmerin. Typically, between about 0.001% and about 10% by weight, preferably between about 0.01% and about 5%, more preferably between about 0.05% and about 2.0% by weight of an antioxidant is present in the pharmaceutical compositions of the invention.

It is understood that certain chelating agents or thiol-containing compounds may also function as antioxidants, for example, tris(2-carboxyethyl) phosphine, cysteine or dithiothreitol. Other types of commonly used antioxidants, however, do not contain a thiol group. It is also understood that certain thiol-containing compounds may also function as a chelating agent, for example, dithiothreitol. Other types of commonly used chelating agents, however, do not contain a thiol group. It is also understood that the pharmaceutical compositions of the instant invention can comprise more than one chelating agent, thiol-containing compound or antioxidant. That is, for example, a chelating agent can be used either alone or in combination with one or more other suitable chelating agents.

Thrombin Peptide Derivative Dimers

In some aspects of the present invention, the NPAR agonists of the methods are thrombin peptide derivative dimers. The dimers essentially do not revert to monomers and still have about the same biological activity as the thrombin peptide derivative monomers described above. A "thrombin peptide derivative dimer" is a molecule comprising two thrombin peptide derivatives (polypeptides) linked by a covalent bond, preferably a disulfide bond between cysteine residues. Thrombin peptide derivative dimers are typically essentially free of the corresponding monomer, e.g., greater than 95% free by weight and preferably greater than 99% free by weight. Preferably the polypeptides are the same and covalently linked through a disulfide bond.

The thrombin peptide derivative dimers of the present invention comprise the thrombin peptide derivatives described above. Specifically, thrombin peptide derivatives have fewer than about fifty amino acids, preferably about thirty-three or fewer amino acids. The thrombin peptide derivative dimers described herein are formed from polypeptides typically having at least six amino acids and preferably from about 12 to about 33 amino acid residues, and more preferably from about 12 to about 23 amino acid residues. Thrombin peptide derivative monomer subunits of the dimers have sufficient homology to the fragment of human thrombin corresponding to thrombin amino acid residues 508-530 (Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6)) so that NPAR is activated.

In a specific embodiment, each of the two thrombin peptide derivatives (monomers) of a dimer comprises the polypeptide Arg-Gly-Asp-Ala-Cys-$X_1$-Gly-Asp-Ser-Gly-Gly-Pro-$X_2$-Val (SEQ ID NO:1), or a C-terminal truncated fragment thereof comprising at least six amino acid residues. More specifically, a polypeptide monomer comprises the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val (SEQ ID NO:6), or a fragment thereof comprising amino acid residues 10-18 of SEQ ID NO: 5. Even more specifically, a polypeptide monomer comprises the polypeptide Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val (SEQ ID NO:2), or a fragment thereof comprising amino acid residues 10-18 of SEQ ID NO:2. $X_1$ is Glu or Gln and $X_2$ is Phe, Met, Leu, His or Val. Preferably $X_1$ is Glu, and $X_2$ is Phe. One example of a polypeptide of this type is the polypeptide Ala-Gly-Tyr-Lys-Pro-Asp-Glu-Gly-Lys-Arg-Gly-Asp-Ala-Cys-Glu-Gly- Asp-Ser-Gly-Gly-Pro-Phe-Val (SEQ ID NO:6). A further example is the polypeptide H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH₂ (SEQ ID NO:3), wherein H signifies a hydrogen atom of alanine indicating no modification at the N-terminus, and NH₂ signifies amidation at the C-terminus as —C(O)NH₂. Zero, one, two or three amino acid residues in the polypeptide differ from the amino acid residue at the corresponding position of SEQ ID NO:6, 1, 2, or 3. Preferably, the difference is conservative.

One example of a thrombin peptide derivative dimer (SEQ ID NO: 3) of the present invention is represented by Formula (IV):

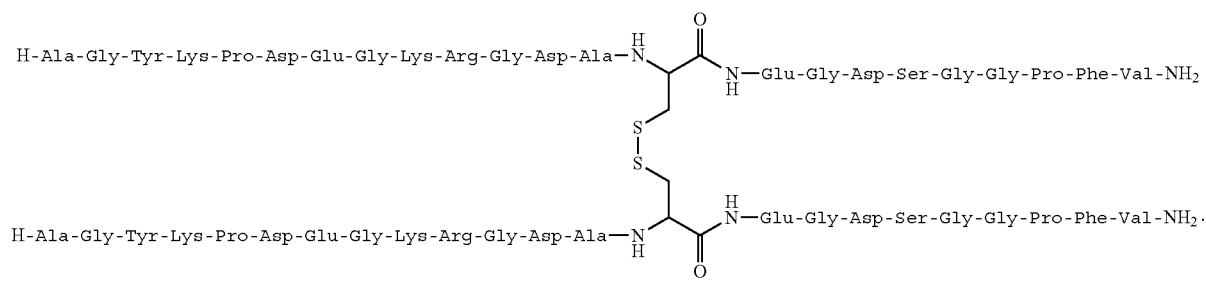

In another specific embodiment, each of the two thrombin peptide derivatives (monomers) of a dimer comprises the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr (SEQ ID NO:27), or a C-terminal truncated fragment thereof having at least twenty-three amino acid residues. More preferably, a polypeptide comprises Ala-Gly-Tyr-Lys-Pro-Asp-Glu-Gly-Lys-Arg-Gly-Asp-Ala-Cys-$X_1$-Gly-Asp-Ser-Gly-Gly-Pro-$X_2$-Val-Met-Lys-Ser-Pro-Phe-Asn-Asn-Arg-Trp-Tyr (SEQ ID NO:8), or a C-terminal truncated fragment thereof comprising at least twenty-three amino acid residues. $X_1$ is Glu or Gln and $X_2$ is Phe, Met, Leu, His or Val. Preferably $X_1$ is Glu, and $X_2$ is Phe. One example of a polypeptide of this type is the polypeptide Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr (SEQ ID NO:27). A further example of a polypeptide of this type is the polypeptide H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-Met-Lys-Ser-Pro-Phe-Asn-Asn-Arg-Trp-Tyr-NH₂ (SEQ ID NO:9), wherein H signifies a hydrogen atom of alanine indicating no modification at the N-terminus, and NH₂ indicates amidation at the C-terminus —C(O)NH₂. Zero, one, two or three amino acid residues in the polypeptide differ from the amino acid residue at the corresponding position of SEQ ID NO:27, 28 or 29. Preferably, the difference is conservative.

Methods of Treatment with NPAR Agonists

A "therapeutically effective amount" for treatment is the quantity of the NPAR agonist that results in an improvement in function, a slowing or arresting of progression, or a reduction in symptoms associated with the disease or disorder, compared to untreated or sham-treated controls. A "therapeutically effective amount" for prophylaxis is the quantity of NPAR agonist that can decrease the probability of developing the disease or disorder.

The amount of the NPAR agonist administered will depend on the degree of severity of the disease or disorder, and will further depend on the release characteristics of the pharmaceutical formulation. It will also depend on the subject's health, size, weight, age, sex and tolerance to drugs. When administered more than once, the NPAR agonists can be administered at evenly spaced intervals. Each dose can be the same or different. A dose can be, for example, 0.1-500 µg, preferably 1-50 µg of NPAR agonist, and is commonly 3, 5, 10, 30 or 50 µg.

NPAR agonists can be administered by any suitable route, including by local introduction. The NPAR agonist can be administered intravenously. The NPAR agonist can be administered to the subject in a sustained release formulation, or can be delivered by a pump or an implantable device, or by an implantable carrier comprising polymers.

Compositions comprising the NPAR agonists (e.g., peptides or peptide dimers) can be administered by any suitable route, including orally, parentally, by inhalation spray, rectally, or topically in dosage unit formulations containing conventional pharmaceutically acceptable carriers, adjuvants, and vehicles. Parental administration includes subcutaneous, intravenous, intra-arterial, intramuscular, intrasternal, intra-tendinous, intraspinal, intracranial, intrathoracic, intraperitoneally, or by infusion techniques. Administration can be by medical instruments.

For parenteral application, particularly suitable vehicles consist of solutions, preferably oily or aqueous solutions, as well as suspensions, emulsions, or implants, including suppositories. Ampules are convenient unit dosages. It will be appreciated that the preferred amounts of active compounds used will vary according to the specific compound being utilized, the particular compositions formulated, the mode of application and the particular site of administration. Optimal administration rates for a given protocol of administration can be readily ascertained by those skilled in the art, using conventional dosage determination tests.

The NPAR agonists can be administered to the subject in conjunction with an acceptable pharmaceutical carrier as part of a pharmaceutical composition. The formulation of the pharmaceutical composition will vary according to the mode of administration selected. Suitable pharmaceutical carriers may contain inert ingredients which do not interact with the active compounds. The carriers should be biocompatible, i.e., non-toxic, non-inflammatory, non-immunogenic and devoid of other undesired reactions at the administration site. Examples of pharmaceutically acceptable carriers and other inert ingredients include, for example, saline, various buffers, alcohol, vegetable oils, polyethylene glycols, gelatin, lactose, sucrose, amylose, magnesium stearate, talc, silicic acid, viscous paraffin, perfume oil, fatty acid monoglycerides and diglycerides, petroethral fatty acid esters, hydroxymethylcellulose, polyvinylpyrrolidone, commercially available inert gels, liquids supplemented with albumin, methyl cellulose, and collagen matrix. Further examples include sterile water, physiological saline, bacteriostatic saline (saline containing about 0.9% mg/ml benzyl alcohol), phosphate-buffered saline, Hank's solution, Ringer's-lactate and the like. Standard pharmaceutical formulation techniques can be employed, such as those described in Remington's Pharmaceutical Sciences (Remington's Pharmaceutical Sciences. 21$^{st}$ edition, Mack Publishing Company, Easton, Pa. (2005)). The pharmaceutical preparations can be sterilized and if desired, mixed with auxiliary agents, e.g., lubricants, preservatives, stabilizers, wetting agents, emulsifiers, salts for influencing osmotic pressure, buffers, colorings and the like which do not deleteriously react with the active compounds.

Pharmaceutical compositions may include gels. Gels are compositions comprising a base selected from an oleaginous base, water, or an emulsion-suspension base. To the base is added a gelling agent which forms a matrix in the base, increasing its viscosity to a semisolid consistency. Examples of gelling agents are hydroxypropyl cellulose, acrylic acid polymers, and the like. The active ingredients are added to the formulation at the desired concentration at a point preceding addition of the gelling agent or can be mixed after the gelation process.

In one embodiment, the NPAR agonists are administered in a sustained release formulation. Polymers are often used to form sustained release formulations. Examples of these polymers include poly α-hydroxy esters such as polylactic acid/polyglycolic acid homopolymers and copolymers, polyphosphazenes (PPHOS), polyanhydrides and poly (propylene fumarates).

Polylactic acid/polyglycolic acid (PLGA) homo and copolymers are well known in the art as sustained release vehicles. The rate of release can be adjusted by the skilled artisan by variation of polylactic acid to polyglycolic acid ratio and the molecular weight of the polymer (see Anderson, et al., *Adv. Drug Deliv. Rev.* 28:5 (1997), the entire teachings of which are incorporated herein by reference). The incorporation of polyethylene glycol into the polymer as a blend to form microparticle carriers allows further alteration of the release profile of the active ingredient (see Cleek, R. L. et al., *J. Control Release* 48:259-268 (1997), the entire teachings of which are incorporated herein by reference). Ceramics such as calcium phosphate and hydroxyapatite can also be incorporated into the formulation to improve mechanical qualities.

PPHOS polymers contain alternating nitrogen and phosphorous with no carbon in the polymer backbone, as shown below in Structural Formula (II):

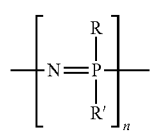

(II)

The properties of the polymer can be adjusted by suitable variation of side groups R and R' that are bonded to the polymer backbone. For example, the degradation of and drug release by PPHOS can be controlled by varying the amount of hydrolytically unstable side groups. With greater incorporation of either imidazolyl or ethylglycol substituted PPHOS, for example, an increase in degradation rate is observed (see Laurencin et al., *J Biomed Mater. Res.* 27:963 (1993), the entire teachings of which are incorporated herein by reference), thereby increasing the rate of drug release.

In certain instances it may be advantageous to co-administer one or more additional pharmacologically active agents along with an NPAR agonist. Depending on the disease or disorder, co-administration with another therapeutic agent may be appropriate, for example, an anesthetic, an analgesic, a steroid, an anti-inflammatory agent, a benzodiazepine derivative, a thrombolytic agent such as tissue plasminogen activator (tPA), or a blood thinning agent such as heparin or coumadin.

Thrombin peptide derivatives and modified thrombin peptide derivatives can be synthesized by solid phase peptide synthesis (e.g., BOC or FMOC) method, by solution phase synthesis, or by other suitable techniques including combinations of the foregoing methods. The BOC and FMOC methods, which are established and widely used, are described in Merrifield, *J. Am. Chem. Soc.* 88:2149 (1963); Meienhofer, *Hormonal Proteins and Peptides*, C. H. Li, Ed., Academic Press, 1983, pp. 48-267; and Barany and Merrifield, in *The Peptides*, E. Gross and J. Meienhofer, Eds., Academic Press, New York, 1980, pp. 3-285. Methods of solid phase peptide synthesis are described in Merrifield, R. B., *Science*, 232: 341 (1986); Carpino, L. A. and Han, G. Y., *J. Org. Chem.*, 37: 3404 (1972); and Gauspohl, H. et al., *Synthesis*, 5: 315 (1992)). The teachings of these six articles are incorporated herein by reference in their entirety.

Thrombin peptide derivative dimers can be prepared by oxidation of the monomer (WO2004/005317). Thrombin peptide derivative dimers can be prepared by reacting the thrombin peptide derivative with an excess of oxidizing agent. A well-known suitable oxidizing agent is iodine.

A "subject" is preferably a human, but can also be an animal in need of treatment with an NPAR agonist, e.g., companion animals (e.g., dogs, cats, and the like), farm animals (e.g., cows, pigs, horses and the like) and laboratory animals (e.g., rats, mice, guinea pigs and the like).

A "non-aromatic heterocyclic group" as used herein, is a non-aromatic carbocyclic ring system that has 3 to 10 atoms and includes at least one heteroatom, such as nitrogen, oxygen, or sulfur. Examples of non-aromatic heterocyclic groups include piperazinyl, piperidinyl, pyrrolidinyl, morpholinyl, thiomorpholinyl.

The term "aryl group" includes both carbocyclic and heterocyclic aromatic ring systems. Examples of aryl groups include phenyl, indolyl, furanyl and imidazolyl.

An "aliphatic group" is a straight chain, branched or cyclic non-aromatic hydrocarbon. An aliphatic group can be completely saturated or contain one or more units of unsaturation (e.g., double and/or triple bonds), but is preferably saturated, i.e., an alkyl group. Typically, a straight chained or branched aliphatic group has from 1 to about 10 carbon atoms, preferably from 1 to about 4, and a cyclic aliphatic group has from 3 to about 10 carbon atoms, preferably from 3 to about 8. Aliphatic groups include, for example, methyl, ethyl, n-propyl, iso-propyl, n-butyl, sec-butyl, tert-butyl, pentyl, cyclopentyl, hexyl, cyclohexyl, octyl and cyclooctyl.

Suitable substituents for an aliphatic group, an aryl group or a non-aromatic heterocyclic group are those which do not significantly lower therapeutic activity of the NPAR agonist, for example, those found on naturally occurring amino acids. Examples include —OH, a halogen (—Br, —Cl, —I and —F), —O($R_e$), —O—CO—($R_e$), —CN, —NO$_2$, —COOH, =O, —NH$_2$, —NH($R_e$), —N($R_e$)$_2$, —COO($R_e$), —CONH$_2$, —CONH($R_e$), —CON($R_e$)$_2$, —SH, —S($R_e$), an aliphatic group, an aryl group and a non-aromatic heterocyclic group.

Each $R_e$ is independently an alkyl group or an aryl group. A substituted aliphatic group can have more than one substituent.

EXAMPLES

Example 1

Oxidative Stress Responses of Human Umbilical Vein Endothelial Cells

Human umbilical vein endothelial cells (HUVECs) were seeded into 12-well plates pre-coated with cell attachment factor at a density of 50,000 cells per well. Cells were allowed to attach overnight, at which point the plating medium was changed to basal medium (EBM), lacking growth factors and antibiotics, but supplemented with insulin-transferrin-selenium (Gibco, Grand Island, N.Y.) to prevent the cells from lifting off the plates during incubation in serum-free medium. After 24 hours, one set of wells was pretreated with 1 ml 10 μg/ml TP508 in EBM for 20 min at 37°. These wells were subsequently treated with 350 μl of 10 μg/ml TP508+100 mM $H_2O_2$. The other wells were treated with 350 μl/well of EBM alone, 100 mM $H_2O_2$, or 10 μg/ml TP508. The treated cells were incubated at 37° for 1 hr, at which point the media was removed and centrifuged for 2 min at 6,000 rpm at room temperature. Duplicate 100 μl aliquots of each supernatant were transferred to flat-bottom 96-well plates, and subjected to the lactate dehydrogenase cytotoxicity detection assay (Boehringer Mannheim, Indianapolis, Ind.). The assay quantifies the activity of lactate dehydrogenase (LDH), released by damaged cells into the culture medium. The results were expressed as the % of cytotoxicity as given by the formula:

% cytotoxicity=(sample activity−low control activity/high control activity−low control activity)*100%.

Low control=LDH activity of cells in EBM alone.

High control=LDH activity of cells lysed by 1% Triton X-100 in EBM.

The results in FIG. 1 suggest that TP508 pretreatment produced rapid changes that protected the cells from the cytotoxic effects of hydrogen peroxide. TP508 may activate glutathione peroxidase, catalase, or NADPH production, which would help glutathione peroxidase convert $H_2O_2$ to water.

Example 2

Apoptosis Studies in B11-C Mouse Fibroblasts

Cells were cultured in serum-free medium for 48 hr, treated with indicated concentrations of TP508 or integrin activating RGD peptides, and then treated for 24 hours with 1.2 mM hydrogen peroxide. Apoptosis was determined by Annexin V and 7-AAD staining using flow microfluorimetry. TP508 has a protective effect, decreasing the number of Annexin V and 7-AAD positive cells, while integrin activating peptides appear to promote apoptosis. See FIGS. 2A and 2B.

Example 3

Gene Array Analysis

A number of gene array analyses have been done using human microvascular endothelial cells (HMVECs). These data have been examined to see if particular mediators of apoptosis were altered by TP508.

Adult and neonatal human microvascular endothelial cells (HMVECs) obtained from Cambrex were plated into flasks coated with cell attachment factor in serum containing medium with growth factor supplements, switched to serum-free medium and cultured in normoxic or hypoxic (1% $O_2$) environments. Twenty-four hours before harvesting, the cells were treated with TP508 or medium alone. Total RNA was extracted and processed for expression analysis using Affymetrics chips.

Heat maps from different sets of these cells all show significant differences in up-regulated genes and down-regulated genes between control and cells treated for 24 hours with TP508. A number of these genes are involved in cell cycle regulation, cell proliferation, and cell death. The reports also show potential signaling pathways that may be involved or utilized by TP508.

Figure 3:
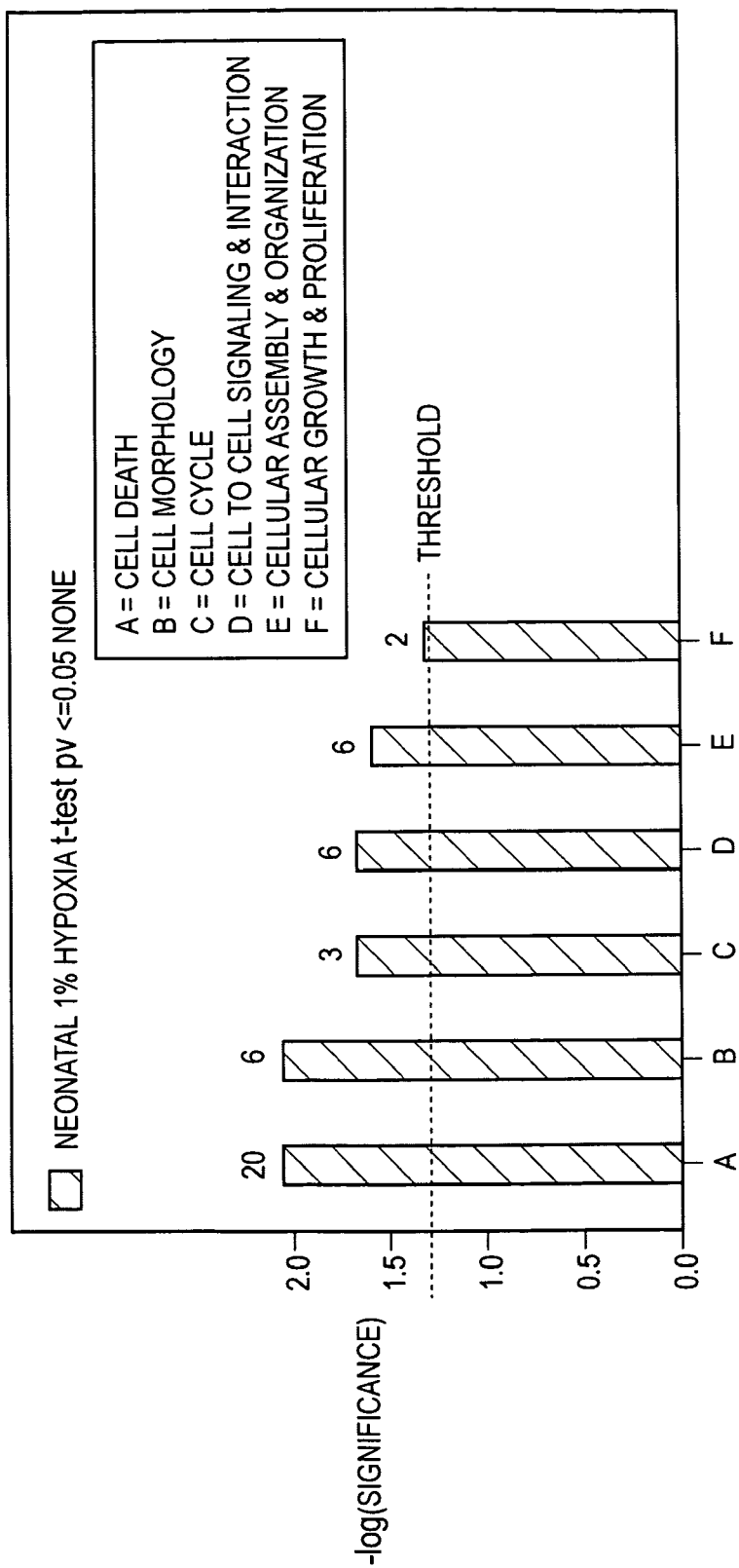
FIG. 3 is a bar graph representing the significance of the differences between levels of gene expression in hypoxic (1% $O_2$) neonatal human microvascular endothelial cells (HMVECs) in the presence versus in the absence of added TP508, for genes in categories A-F. The numbers on the bars represent the number of input genes on these functional process and canonical pathways. (Genes expressed due to hypoxic condition t test p-value <=0.05.) (p<0.05; 999 genes; n=4)

In neonatal HMVECs, TP508 produced effects on stress related pathways that are high in hypoxic cells, but reduced due to TP508 treatment. TP508 significantly changed expression of 20 genes associated with cell death and others associated with cell morphology, cell cycle, and cell signaling. See FIG. 3.

Figure 4:
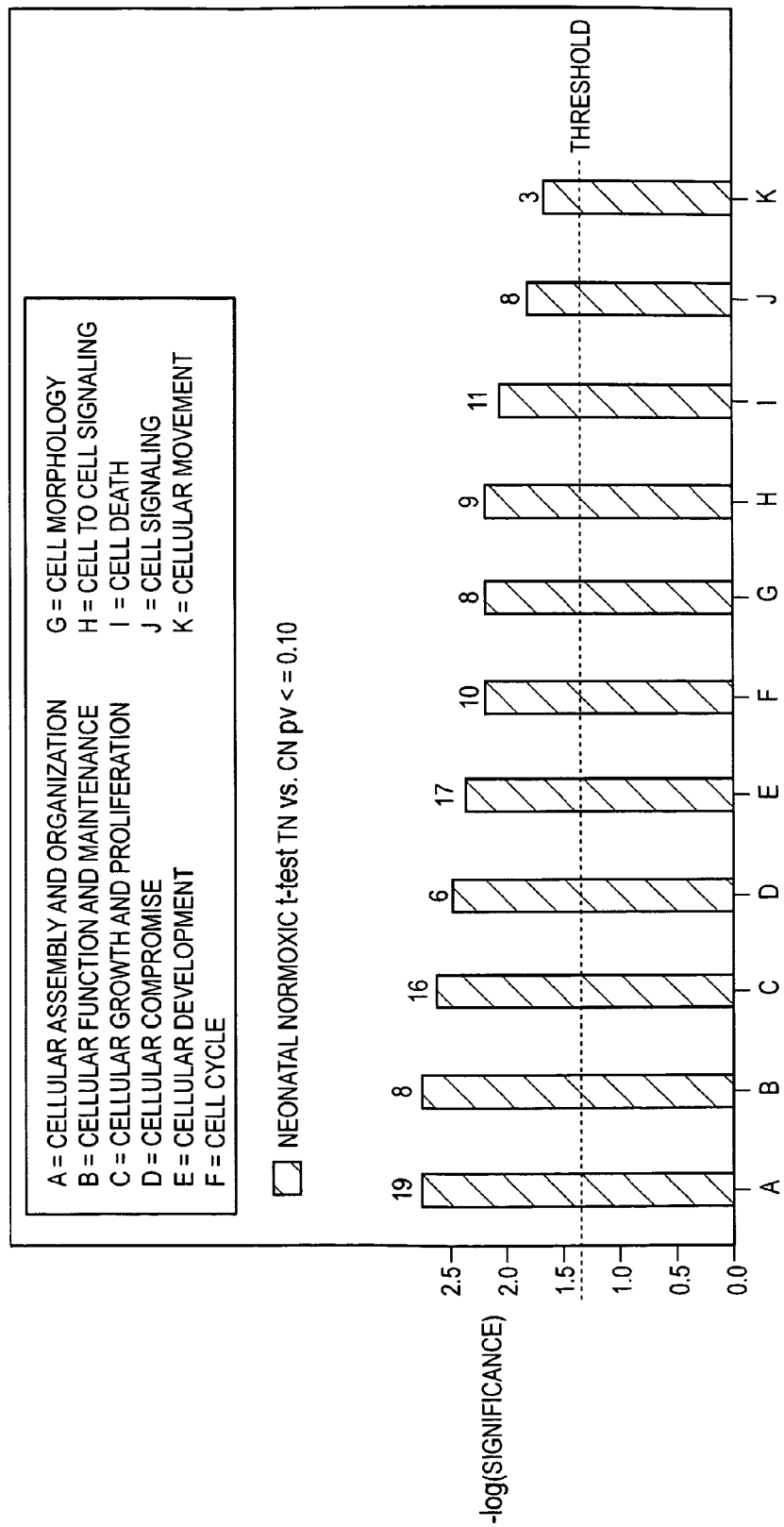
FIG. 4 is a bar graph representing the significance of the differences between levels of gene expression in hypoxic (1% $O_2$) neonatal human microvascular endothelial cells (HMVECs) in the presence versus in the absence of added TP508, for genes in categories A-K. The numbers on the bars represent the number of input genes on these functional process and canonical pathways. (Genes expressed due to hypoxic condition t test p-value <=0.10.) (p<0.01; 82 genes; n=4)

Several different signaling pathways appear to be activated by TP508. The signal pathways with the highest potential significance based on this limited gene set (4 and 5 genes out of 82 for each pathway) were EGF, IL4, IL2, VEGF, FGF, and IGF. Among genes affecting developmental processes and function, the most genes (11 and 12) are involved in hematological and skeletal/muscular systems. Cellular process genes suggest effects on cell organization, maintenance, growth/proliferation, development, cell cycle, cell morphology, cell signaling, cell death, and movement. See FIG. 4.

Figure 5:
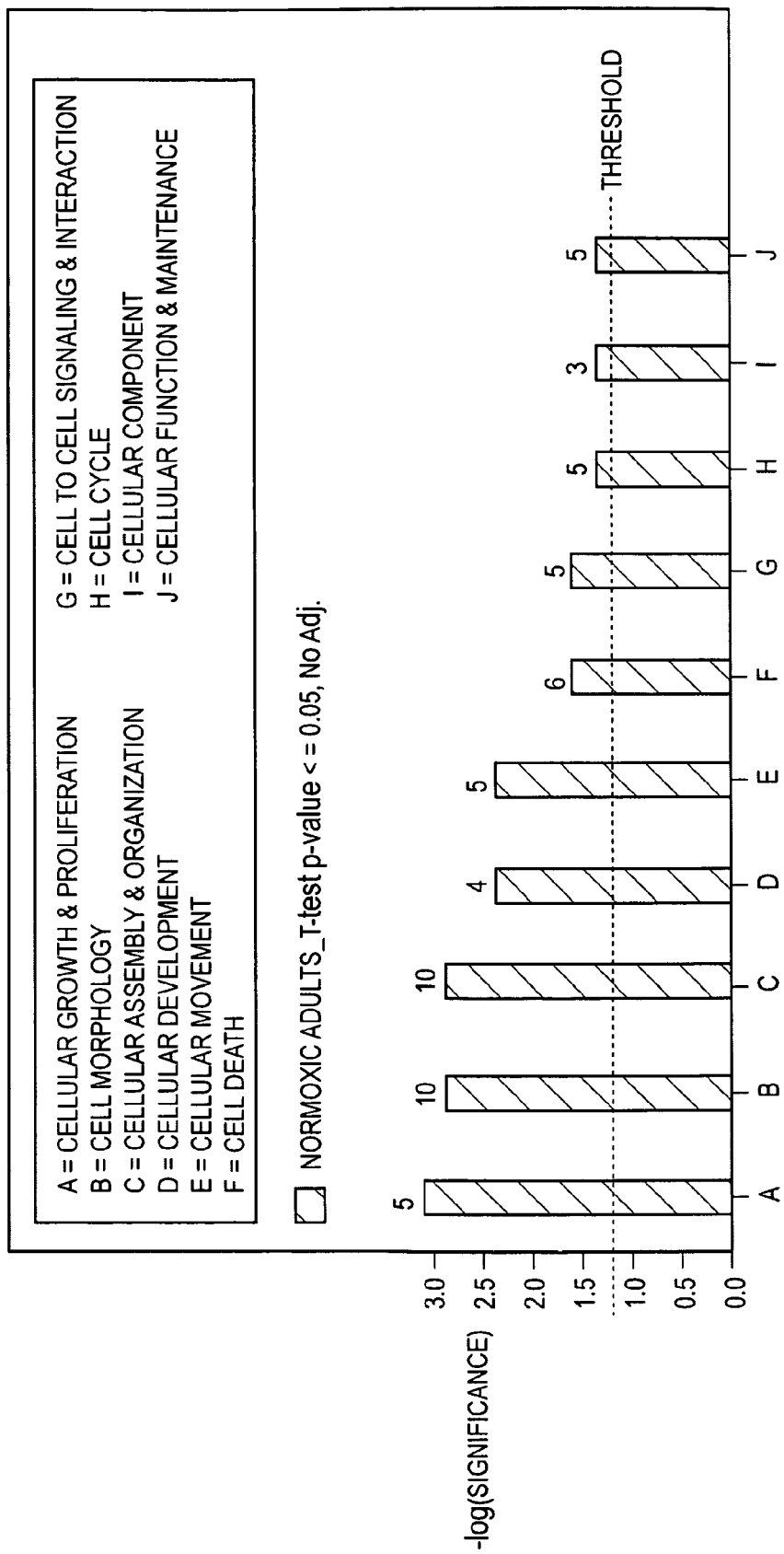
FIG. 5 is a bar graph representing the significance of the differences between levels of gene expression in hypoxic (1% $O_2$) adult human microvascular endothelial cells (HMVECs) in the presence versus in the absence of added TP508, for genes in categories A-J. The numbers on the bars represent the number of input genes on these functional process and canonical pathways. (Genes expressed due to hypoxic condition t test p-value <=0.05.) (p<0.05; 418 genes)

In adult hypoxic HMVECs, (1% $O_2$) the most significant cellular processes affected by TP508 were growth/proliferation, cell assembly, cell movement, cell signaling, and cell components. See FIG. 5. A number of genes that significantly changed were related to injury. Significant gene expression changes were noted that related to PPAR signaling and estrogen receptor signaling, but not to signaling through insulin receptors, ERK/MAPk signaling, or integrin signaling. The capsase-1 dominant-negative inhibitor pseudo-ICE appeared to be down-regulated by hypoxia, but significantly up-regulated by TP508 treatment of these hypoxic cells. CRCR1 or DDC that induces apoptosis (Fume, C. et al., Proc Natl Acad Sci USA 103:4128-4133, 2006), is up-regulated by hypoxia, but down-regulated or returned to normal levels when hypoxic cells are treated with TP508.

Another example of a gene with a pattern similar to DDC is the PH domain and leucine rich repeat protein phosphatase (PHLPP) that de-phosphorylates AKT. AKT is phosphorylated by a number of survival factors and is a key regulator for preventing apoptosis. By up-regulation or activation of PHLPP, AKT is dephosphorylated to induce apoptosis (Gao, T. et al., Mol Cell 18(1):13-24, 2005). In HMVECs, hypoxia up-regulates PHLPP, but TP508 treatment of hypoxic cells down-regulates the expression of this phosphatase.

Example 4

Apoptosis Genes in HCAE Cells

Gene array data has been collected using human coronary artery endothelial (HCAE) cells. These studies have focused on the effects of TNFα and the ability of TP508 to prevent or reverse the effects of TNFα. TNFα is known to induce apoptosis in a number of cell types including endothelial cells.

These gene array data in HCAE cells have been analyzed for genes that cluster to a specific profile. In this case, we only looked at genes that were up-regulated by TNFα more than 3-fold, but were not significantly up-regulated by TP508 or TNFα when these cells are treated with TP508. In the set of data studied, over a thousand genes fall into this cluster profile and appear to be up-regulated by more than 3-fold by TNFα treatment alone, but are not upregulated by TNFα if the cells are pretreated with TP508. Of these, 35 gene sets representing more than 30 genes are specifically involved in induction of apoptosis.

While this invention has been particularly shown and described with references to example embodiments thereof, it will be understood by those skilled in the art that various changes in form and details may be made therein without departing from the scope of the invention encompassed by the appended claims.

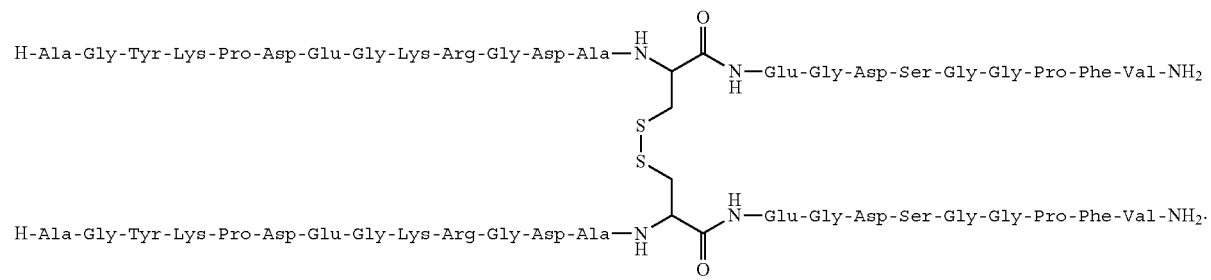

What is claimed is:

1. A method for treating a disease or disorder in a subject, the method comprising administering to the subject a therapeutically effective amount of an agonist of a non-proteolytically activated thrombin receptor, wherein the disease or disorder is selected from the group consisting of: scleroderma, macular degeneration, diabetic retinopathy, closed head trauma, glaucoma, optic neuritis, and allograft vasculopathy.

2. The method of claim 1, wherein the disease or disorder is glaucoma.

3. The method of claim 1, wherein the disease or disorder is closed head trauma.

4. The method of claim 1, wherein the disease or disorder is optic neuritis.

5. The method of claim 1, wherein the disease or disorder is scleroderma.

6. The method of claim 1, wherein the agonist is a thrombin peptide derivative comprising the amino acid sequence Asp-Ala-R, wherein R is a serine esterase conserved sequence; and wherein the thrombin peptide derivative comprises from about 12 to about 23 amino acid residues.

7. The method of claim 6, wherein the thrombin peptide derivative comprises an N-terminus which is unsubstituted, and a C-terminus which is unsubstituted or a C-terminal amide represented by —C(O)NH$_2$.

8. The method of claim 7, wherein the thrombin peptide derivative comprises the polypeptide Arg-Gly-Asp-Ala-Cys-X$_1$-Gly-Asp-Ser-Gly-Gly-Pro-X$_2$-Val (SEQ ID NO:1), wherein X$_1$ is Glu or Gln and X$_2$ is Phe, Met, Leu, His or Val.

9. The method of claim 7, wherein the thrombin peptide derivative comprises the polypeptide Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), an N-terminal truncated fragment of the thrombin peptide derivative having at least fourteen amino acid residues, or a C-terminal truncated fragment of the thrombin peptide derivative having at least eighteen amino acid residues, wherein X$_1$ is Glu or Gln and X$_2$ is Phe, Met, Leu, His or Val.

10. The method of claim 1, wherein the agonist is the polypeptide H-Ala-Gly-Tyr-Lys-Pro-Asp-Glu-Gly-Lys-Arg-Gly-Asp-Ala-Cys-Glu-Gly-Asp-Ser-Gly-Gly-Pro-Phe-Val-NH$_2$ (SEQ ID NO:3).

11. The method of claim 7, wherein the thrombin peptide derivative comprises the polypeptide Ala-Gly-Tyr-Lys-Pro-Asp-Glu-Gly-Lys-Arg-Gly-Asp-Ala-Xaa-X$_1$-Gly-Asp-Ser-Gly-Gly-Pro-X$_2$-Val (SEQ ID NO:5) or a fragment thereof comprising amino acids 10-18 of SEQ ID NO:5, wherein Xaa is alanine, glycine, serine or an S-protected cysteine; X$_1$ is Glu or Gln; and X$_2$ is Phe, Met, Leu, His or Val.

12. The method of claim 1, wherein the agonist is a peptide dimer comprising two thrombin peptide derivatives 12 to 23 amino acid residues in length which, independently, comprise the polypeptide Asp-Ala-Cys-X$_1$-Gly-Asp-Ser-Gly-Gly-Pro-X$_2$-Val (SEQ ID NO:10), wherein X$_1$ is Glu or Gln and X$_2$ is Phe, Met, Leu, His or Val, or a C-terminal truncated fragment thereof having at least six amino acid residues, provided that zero, one, two, or three amino acid residues in the polypeptide differ from those residues in the corresponding position of SEQ ID NO:10; said thrombin peptide derivatives optionally comprising a C-terminal amide; and said thrombin peptide derivatives optionally comprising an acylated N-terminus; and the dimer is essentially free of monomer;

the thrombin peptide derivatives are the same;

the thrombin peptide derivatives are covalently linked through a disulfide bond;

and the thrombin peptide derivatives consist of from about 12 to about 23 amino acids.

13. The method of claim 12, wherein the thrombin peptide derivatives each comprise an N-terminus which is unsubstituted; and a C-terminus which is unsubstituted or a C-terminal amide represented by —C(O)NH$_2$.

14. The method of claim 13, wherein the thrombin peptide derivatives comprise the polypeptide Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), wherein X$_1$ is Glu or Gln and X$_2$ is Phe, Met, Leu, His or Val or a fragment thereof comprising amino acid residues 10-18 of SEQ ID NO:2.

15. The method of claim 13, wherein the thrombin peptide derivatives comprise the polypeptide Ala-Gly-Tyr-Lys-Pro-Asp-Glu-Gly-Lys-Arg-Gly-Asp-Ala-Cys-X$_1$-Gly-Asp-Ser-Gly-Gly-Pro-X$_2$-Val (SEQ ID NO:2), wherein X$_1$ is Glu or Gln and X$_2$ is Phe, Met, Leu, His or Val.

16. The method of claim 1, wherein the agonist is a peptide dimer of (SEQ ID NO: 3) represented by the following structural formula: